(12) United States Patent
Lilius et al.

(10) Patent No.: US 6,866,995 B1
(45) Date of Patent: Mar. 15, 2005

(54) METHOD TO ENABLE ASSESSMENT OF GROWTH AND DEATH OF MICRO-ORGANISMS

(76) Inventors: Esa-Matti Lilius, Vaakunatie 10, Kaarina (FI), FIN-20780; Marko Virta, Kauppiaskatu 10 D 59, Turku (FI), FIN-20100

( * ) Notice: Subject to any disclaimer, the term of this patent is extended or adjusted under 35 U.S.C. 154(b) by 152 days.

(21) Appl. No.: 09/980,585

(22) PCT Filed: Jun. 7, 2000

(86) PCT No.: PCT/FI00/00507

§ 371 (c)(1),
(2), (4) Date: Mar. 4, 2002

(87) PCT Pub. No.: WO00/75367

PCT Pub. Date: Dec. 14, 2000

(30) Foreign Application Priority Data

Jun. 7, 1999 (FI) .................................................. 991296

(51) Int. Cl.[7] ............................ C12Q 1/00; C12Q 1/02; C12Q 1/24; C12Q 1/66
(52) U.S. Cl. ................................ 435/4; 435/8; 435/29; 435/30
(58) Field of Search ............................ 435/4, 8, 29, 30, 435/7.1, 419, 7.23, 69.1, 199, 91.2, 196, 6, 252.3, 465, 456, 183, 415, 320.1, 426, 325, 235.1; 514/44; 530/350, 300; 536/23.1, 24.3; 702/19, 20; 436/518, 24.3, 25.32; 800/312, 314; 424/94.1

(56) References Cited

U.S. PATENT DOCUMENTS

| 5,164,301 A | 11/1992 | Thompson et al. |
| 5,824,468 A | 10/1998 | Scherer et al. |
| 5,976,796 A | * 11/1999 | Szalay et al. .................. 435/6 |
| 6,143,502 A | * 11/2000 | Grentzmann et al. .......... 435/6 |

FOREIGN PATENT DOCUMENTS

| JP | 11146798 A | 6/1999 |
| WO | WO 96/23898 A1 | 8/1996 |
| WO | WO 98/14605 A1 | 4/1998 |
| WO | WO 98/30715 A1 | 7/1998 |

OTHER PUBLICATIONS

Fratamico, P.M. et al. Construction and characterization of *Escherichia coli* 0157:H7 strains expressing firefly luciferase and green fluorescent protein and their use in survival studies. 1997. vol. 60(10):1167–1173.*

Brovko, L.Y. et al. Sensitivity of detection of bacteria with fluorescent and luminescent phenotypes using different instruments. 2000. In Optical Diagnostics of Living Cells III, Daniel L. Farkas, Robert C. Leif, eds. Pro. of SPIE vol. 3921:147–156.*

Wang, Y. et al. The Renilla luciferase–modified GFP fusion proteins is functional in transformed cells. Oct. 1996. Pro. of the 9th Int. Sym. on Bioluminescence and chemiluminescence, Woods Hole, Mass. John Wiley & Sons, Chichester, UK. pp. 419–422.*

* cited by examiner

*Primary Examiner*—Mark Navarro
(74) *Attorney, Agent, or Firm*—Rothwell, Figg, Ernst & Manbeck, P.C.

(57) ABSTRACT

The invention is a method of assessing growth and death rates of micro-organisms within a time period environment of interest. Two reporter genes coding for luminescent and/or fluorescent products introduced into the micro-organism produce at least two products which luminesce or fluoresce. They include, either an essentially stable product produced in an essentially known proportion to the total amount of cells of the micro-organism that are or have been alive within a time period, a product present in an essentially known proportion to the amount of cells alive at any moment within the time period, or an essentially stable product produced in an essentially known proportion to the total amount of cells of the micro-organism that have died within the time period. The micro-organism is incubated and luminescence and/or fluorescence is detected after at time period. Finally, the growth and death rates of the micro-organism are assessed.

10 Claims, 5 Drawing Sheets

SEQUENCE LISTING

```
<160> NUMBER OF SEQ ID NOS: 4

<210> SEQ ID NO 1
<211> LENGTH: 5051
<212> TYPE: DNA
<213> ORGANISM: Artificial Sequence
<220> FEATURE:
<223> OTHER INFORMATION: pGFP+Luc* plasmid
<220> FEATURE:
<221> NAME/KEY: promoter
<222> LOCATION: (95)..(199)
<223> OTHER INFORMATION: lac promoter
<220> FEATURE:
<221> NAME/KEY: gene
<222> LOCATION: (289)..(1005)
<223> OTHER INFORMATION: Coding sequence for GFP
<220> FEATURE:
```

-continued

```
<221> NAME/KEY: gene
<222> LOCATION: (1044)..(2693)
<223> OTHER INFORMATION: coding sequence for firefly luciferase
<220> FEATURE:
<221> NAME/KEY: gene
<222> LOCATION: (3251)..(4108)
<223> OTHER INFORMATION: coding sequence for beta-lactamase

<400> SEQUENCE: 1
```

| | | | | | |
|---|---|---|---|---|---|
| agcgcccaat | acgcaaaccg | cctctccccg | cgcgttggcc | gattcattaa | tgcagctggc | 60 |
| acgacaggtt | tcccgactgg | aaagcgggca | gtgagcgcaa | cgcaattaat | gtgagttagc | 120 |
| tcactcatta | ggcaccccag | gctttacact | ttatgcttcc | ggctcgtatg | ttgtgtggaa | 180 |
| ttgtgagcgg | ataacaattt | cacacaggaa | acagctatga | ccatgattac | gccaagcttg | 240 |
| catgcctgca | ggtcgactct | agaggatccc | gggtaccgg | tcgccaccat | ggtgagcaag | 300 |
| ggcgaggagc | tgttcaccgg | ggtggtgccc | atcctggtcg | agctggacgg | cgacgtaaac | 360 |
| ggccacaagt | tcagcgtgtc | cggcgagggc | gagggcgatg | ccacctacgg | caagctgacc | 420 |
| ctgaagttca | tctgcaccac | cggcaagctg | cccgtgccct | ggcccaccct | cgtgaccacc | 480 |
| ctgacctacg | gcgtgcagtg | cttcagccgc | taccccgacc | acatgaagca | gcacgacttc | 540 |
| ttcaagtccg | ccatgcccga | aggctacgtc | caggagcgca | ccatcttctt | caaggacgac | 600 |
| ggcaactaca | agacccgcgc | cgaggtgaag | ttcgagggcg | acaccctggt | gaaccgcatc | 660 |
| gagctgaagg | gcatcgactt | caaggaggac | ggcaacatcc | tggggcacaa | gctggagtac | 720 |
| aactacaaca | gccacaacgt | ctatatcatg | gccgacaagc | agaagaacgg | catcaaggtg | 780 |
| aacttcaaga | tccgccacaa | catcgaggac | ggcagcgtgc | agctcgccga | ccactaccag | 840 |
| cagaacaccc | ccatcggcga | cggccccgtg | ctgctgcccg | acaaccacta | cctgagcacc | 900 |
| cagtccgccc | tgagcaaaga | ccccaacgag | aagcgcgatc | acatggtcct | gctggagttc | 960 |
| gtgaccgccg | ccgggatcac | tctcggcatg | gacgagctgt | acaagtaaag | cggccgctct | 1020 |
| agaactagtg | gatcccccgt | accatggaag | acgccaaaaa | cataaagaaa | ggcccggcgc | 1080 |
| cattctatcc | gctagaggat | ggaaccgctg | gagagcaact | gcataaggct | atgaagagat | 1140 |
| acgccctggt | tcctggaaca | attgctttta | cagatgcaca | tatcgaggtg | aacatcacgt | 1200 |
| acgcggaata | cttcgaaatg | tccgttcggt | tggcagaagc | tatgaaacga | tatgggctga | 1260 |
| atacaaatca | cagaatcgtc | gtatgcagtg | aaaactctct | tcaattcttt | atgccggtgt | 1320 |
| tgggcgcgtt | atttatcgga | gttgcagttg | cgcccgcgaa | cgacatttat | aatgaacgtg | 1380 |
| aattgctcaa | cagtatgaac | atttcgcagc | ctaccgtagt | gtttgtttcc | aaaaagggt | 1440 |
| tgcaaaaaat | tttgaacgtg | caaaaaaaat | taccaataat | ccagaaaatt | attatcatgg | 1500 |
| attctaaaac | ggattaccag | ggatttcagt | cgatgtacac | gttcgtcaca | tctcatctac | 1560 |
| ctcccggttt | taatgaatac | gattttgtac | cagagtcctt | tgatcgtgac | aaaacaattg | 1620 |
| cactgataat | gaactcctct | ggatctactg | ggttacctaa | gggtgtggcc | cttccgcata | 1680 |
| gaactgcctg | cgtcagattc | tcgcatgcca | gagatcctat | ttttggcaat | caaatcattc | 1740 |
| cggatactgc | gattttaagt | gttgttccat | tccatcacgg | ttttggaatg | tttactacac | 1800 |
| tcggatattt | gatatgtgga | tttcgagtcg | tcttaatgta | tagatttgaa | gaagagctgt | 1860 |
| ttttacgatc | ccttcaggat | tacaaaattc | aaagtgcgtt | gctagtacca | accctatttt | 1920 |
| cattcttcgc | caaaagcact | ctgattgaca | aatacgattt | atctaattta | cacgaaattg | 1980 |
| cttctggggg | cgcacctctt | tcgaaagaag | tcggggaagc | ggttgcaaaa | cgcttccatc | 2040 |
| ttccagggat | acgacaagga | tatgggctca | ctgagactac | atcagctatt | ctgattacac | 2100 |

-continued

```
ccgaggggga tgataaaccg ggcgcggtcg gtaaagttgt tccattttt gaagcgaagg    2160 ttgtggatct ggataccggg aaaacgctgg gcgttaatca gagaggcgaa ttatgtgtca   2220
gaggacctat gattatgtcc ggttatgtaa acaatccgga agcgaccaac gccttgattg   2280
acaaggatgg atggctacat tctggagaca tagcttactg ggacgaagac gaacacttct   2340
tcatagttga ccgcttgaag tctttaatta aatacaaagg ataccaggtg gccccgctg    2400 aattggagtc gatattgtta caacacccca acatcttcga cgcgggcgtg gcaggtcttc   2460
ccgacgatga cgccggtgaa cttcccgccg ccgttgttgt tttggagcac ggaaagacga   2520
tgacggaaaa agagatcgtg gattacgtcg ccagtcaagt aacaaccgcc aaaaagttgc   2580
gcggaggagt tgtgtttgtg gacgaagtac cgaaaggtct taccgaaaaa ctcgacgcaa   2640
gaaaaatcag agagatcctc ataaaggcca gaagggcgg aaagtccaaa ttgtaaaatg     2700
taactgtatt cagcgatgac gaaattctta gctattgtaa tactctaggg gctgcaggaa   2760
ttcgatatca agcttatcga taccgtcgac ctcgaggggg ggcccttttcg tctcgcgcgt   2820 ttcggtgatg acggtgaaaa cctctgacac atgcagctcc cggagacggt cacagcttgt   2880
ctgtaagcgg atgccgggag cagacaagcc cgtcagggcg cgtcagcggg tgttggcggg   2940
tgtcggggct ggcttaacta tgcggcatca gagcagattg tactgagagt gcaccatatg   3000
cggtgtgaaa taccgcacag atgcgtaagg agaaaatacc gcatcaggcg ccttaaggg    3060 cctcgtgata cgcctatttt tataggttaa tgtcatgata ataatggttt cttagacgtc   3120
aggtggcact tttcgggaa atgtgcgcgg aaccctatt tgtttatttt tctaaataca     3180
ttcaaatatg tatccgctca tgagacaata accctgataa atgcttcaat aatattgaaa   3240
aaggaagagt atgagtattc aacatttccg tgtcgccctt attccctttt ttgcggcatt   3300
ttgccttcct gtttttgctc acccagaaac gctggtgaaa gtaaaagatg ctgaagatca   3360
gttgggtgca cgagtgggtt acatcgaact ggatctcaac agcggtaaga tccttgagag   3420
ttttcgcccc gaagaacgtt ttccaatgat gagcactttt aaagttctgc tatgtggcgc   3480
ggtattatcc cgtattgacg ccgggcaaga gcaactcggt cgccgcatac actattctca   3540
gaatgacttg gttgagtact caccagtcac agaaaagcat cttacggatg gcatgacagt   3600
aagagaatta tgcagtgctg ccataaccat gagtgataac actgcggcca acttacttct   3660
gacaacgatc ggaggaccga aggagctaac cgcttttttg cacaacatgg gggatcatgt   3720
aactcgcctt gatcgttggg aaccggagct gaatgaagcc ataccaaacg acgagcgtga   3780
caccacgatg cctgtagcaa tggcaacaac gttgcgcaaa ctattaactg gcgaactact   3840
tactctagct tcccggcaac aattaataga ctggatggag gcggataaag ttgcaggacc   3900
acttctgcgc tcggcccttc cggctggctg gtttattgct gataaatctg gagccggtga   3960
gcgtgggtct cgcggtatca ttgcagcact ggggccagat ggtaagccct cccgtatcgt   4020
agttatctac acgacgggga gtcaggcaac tatggatgaa cgaaatagac agatcgctga   4080
gataggtgcc tcactgatta agcattggta actgtcagac caagtttact catatatact   4140
ttagattgat ttaaaacttc attttttaatt taaaaggatc taggtgaaga tccttttga   4200 taatctcatg accaaaatcc cttaacgtga gttttcgttc cactgagcgt cagacccccgt   4260 agaaaagatc aaaggatctt cttgagatcc ttttttttctg cgcgtaatct gctgcttgca   4320
aacaaaaaaa ccaccgctac cagcggtggt ttgtttgccg gatcaagagc taccaactct   4380
ttttccgaag gtaactggct tcagcagagc gcagatacca aatactgtcc ttctagtgta   4440
```

-continued

```
gccgtagtta ggccaccact tcaagaactc tgtagcaccg cctacatacc tcgctctgct    4500
aatcctgtta ccagtggctg ctgccagtgg cgataagtcg tgtcttaccg ggttggactc    4560
aagacgatag ttaccggata aggcgcagcg gtcgggctga acgggggggtt cgtgcacaca    4620 gcccagcttg gagcgaacga cctacaccga actgagatac ctacagcgtg agctatgaga    4680
aagcgccacg cttcccgaag ggagaaaggc ggacaggtat ccggtaagcg gcagggtcgg    4740
aacaggagag cgcacgaggg agcttccagg gggaaacgcc tggtatcttt atagtcctgt    4800
cgggtttcgc cacctctgac ttgagcgtcg attttttgtga tgctcgtcag ggggggcggag    4860 cctatggaaa aacgccagca acgcggcctt tttacggttc ctggccttttt gctggccttt    4920 tgctcacatg ttctttcctg cgttatcccc tgattctgtg ataaccgta ttaccgcctt    4980 tgagtgagct gataccgctc gccgcagccg aacgaccgag cgcagcgagt cagtgagcga    5040
ggaagcggaa g                                                        5051
```

<210> SEQ ID NO 2
<211> LENGTH: 239
<212> TYPE: PRT
<213> ORGANISM: Unknown
<220> FEATURE:
<223> OTHER INFORMATION: source of GFP unknown

<400> SEQUENCE: 2

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 3

-continued

```
<211> LENGTH: 550
<212> TYPE: PRT
<213> ORGANISM: Unknown
<220> FEATURE:
<223> OTHER INFORMATION: source of firefly luciferase unknown

<400> SEQUENCE: 3
```

| Met | Glu | Asp | Ala | Lys | Asn | Ile | Lys | Lys | Gly | Pro | Ala | Pro | Phe | Tyr | Pro |
|---|---|---|---|---|---|---|---|---|---|---|---|---|---|---|---|
| 1 | | | | 5 | | | | | 10 | | | | | 15 | |

| Leu | Glu | Asp | Gly | Thr | Ala | Gly | Glu | Gln | Leu | His | Lys | Ala | Met | Lys | Arg |
| | | | 20 | | | | | 25 | | | | | 30 | | |

| Tyr | Ala | Leu | Val | Pro | Gly | Thr | Ile | Ala | Phe | Thr | Asp | Ala | His | Ile | Glu |
| | | 35 | | | | | 40 | | | | | 45 | | | |

| Val | Asn | Ile | Thr | Tyr | Ala | Glu | Tyr | Phe | Glu | Met | Ser | Val | Arg | Leu | Ala |
| | 50 | | | | | 55 | | | | | 60 | | | | |

| Glu | Ala | Met | Lys | Arg | Tyr | Gly | Leu | Asn | Thr | Asn | His | Arg | Ile | Val | Val |
| 65 | | | | | 70 | | | | | 75 | | | | | 80 |

| Cys | Ser | Glu | Asn | Ser | Leu | Gln | Phe | Phe | Met | Pro | Val | Leu | Gly | Ala | Leu |
| | | | | 85 | | | | | 90 | | | | | 95 | |

| Phe | Ile | Gly | Val | Ala | Val | Ala | Pro | Ala | Asn | Asp | Ile | Tyr | Asn | Glu | Arg |
| | | | 100 | | | | | 105 | | | | | 110 | | |

| Glu | Leu | Leu | Asn | Ser | Met | Asn | Ile | Ser | Gln | Pro | Thr | Val | Val | Phe | Val |
| | | 115 | | | | | 120 | | | | | 125 | | | |

| Ser | Lys | Lys | Gly | Leu | Gln | Lys | Ile | Leu | Asn | Val | Gln | Lys | Lys | Leu | Pro |
| | 130 | | | | | 135 | | | | | 140 | | | | |

| Ile | Ile | Gln | Lys | Ile | Ile | Ile | Met | Asp | Ser | Lys | Thr | Asp | Tyr | Gln | Gly |
| 145 | | | | | 150 | | | | | 155 | | | | | 160 |

| Phe | Gln | Ser | Met | Tyr | Thr | Phe | Val | Thr | Ser | His | Leu | Pro | Pro | Gly | Phe |
| | | | | 165 | | | | | 170 | | | | | 175 | |

| Asn | Glu | Tyr | Asp | Phe | Val | Pro | Glu | Ser | Phe | Asp | Arg | Asp | Lys | Thr | Ile |
| | | | 180 | | | | | 185 | | | | | 190 | | |

| Ala | Leu | Ile | Met | Asn | Ser | Ser | Gly | Ser | Thr | Gly | Leu | Pro | Lys | Gly | Val |
| | | 195 | | | | | 200 | | | | | 205 | | | |

| Ala | Leu | Pro | His | Arg | Thr | Ala | Cys | Val | Arg | Phe | Ser | His | Ala | Arg | Asp |
| | 210 | | | | | 215 | | | | | 220 | | | | |

| Pro | Ile | Phe | Gly | Asn | Gln | Ile | Ile | Pro | Asp | Thr | Ala | Ile | Leu | Ser | Val |
| 225 | | | | | 230 | | | | | 235 | | | | | 240 |

| Val | Pro | Phe | His | His | Gly | Phe | Gly | Met | Phe | Thr | Thr | Leu | Gly | Tyr | Leu |
| | | | | 245 | | | | | 250 | | | | | 255 | |

| Ile | Cys | Gly | Phe | Arg | Val | Val | Leu | Met | Tyr | Arg | Phe | Glu | Glu | Glu | Leu |
| | | | 260 | | | | | 265 | | | | | 270 | | |

| Phe | Leu | Arg | Ser | Leu | Gln | Asp | Tyr | Lys | Ile | Gln | Ser | Ala | Leu | Leu | Val |
| | | 275 | | | | | 280 | | | | | 285 | | | |

| Pro | Thr | Leu | Phe | Ser | Phe | Phe | Ala | Lys | Ser | Thr | Leu | Ile | Asp | Lys | Tyr |
| | 290 | | | | | 295 | | | | | 300 | | | | |

| Asp | Leu | Ser | Asn | Leu | His | Glu | Ile | Ala | Ser | Gly | Gly | Ala | Pro | Leu | Ser |
| 305 | | | | | 310 | | | | | 315 | | | | | 320 |

| Lys | Glu | Val | Gly | Glu | Ala | Val | Ala | Lys | Arg | Phe | His | Leu | Pro | Gly | Ile |
| | | | | 325 | | | | | 330 | | | | | 335 | |

| Arg | Gln | Gly | Tyr | Gly | Leu | Thr | Glu | Thr | Thr | Ser | Ala | Ile | Leu | Ile | Thr |
| | | | 340 | | | | | 345 | | | | | 350 | | |

| Pro | Glu | Gly | Asp | Asp | Lys | Pro | Gly | Ala | Val | Gly | Lys | Val | Val | Pro | Phe |
| | | 355 | | | | | 360 | | | | | 365 | | | |

| Phe | Glu | Ala | Lys | Val | Val | Asp | Leu | Asp | Thr | Gly | Lys | Thr | Leu | Gly | Val |
| | 370 | | | | | 375 | | | | | 380 | | | | |

-continued

```
Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Asp Glu His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 4
<211> LENGTH: 286
<212> TYPE: PRT
<213> ORGANISM: Unknown
<220> FEATURE:
<223> OTHER INFORMATION: source of beta-lactamase unknown

<400> SEQUENCE: 4

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
                35                  40                  45

Leu Asn Ser Gly Lys Ile Leu Glu Ser Phe Arg Pro Glu Glu Arg Phe
50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
                100                 105                 110

Asp Gly Met Thr Val Arg Glu Leu Cys Ser Ala Ala Ile Thr Met Ser
                115                 120                 125

Asp Asn Thr Ala Ala Asn Leu Leu Leu Thr Thr Ile Gly Gly Pro Lys
130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
                180                 185                 190
```

-continued

```
Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
        210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

METHOD TO ENABLE ASSESSMENT OF GROWTH AND DEATH OF MICRO-ORGANISMS

CROSS-REFERENCE TO RELATED APPLICATION

The present application is a national stage filing under 35 U.S.C. §371 of PCT/FI00/00507 filed on 7 Jun. 2000 and claims priority under 35 U.S.C. §119 to Finland patent application No. 991296 filed on 7 Jun. 1999.

This invention relates to a method to enable the assessment of growth and death of a micro-organism within a chosen time period in an environment of interest.

BACKGROUND OF THE INVENTION

When studying growth and death of a micro-organism under the influence of specific environments, e.g. production and storage environments that e.g. could or could not be refrigerated, or involving chemicals or matrixes, e.g. antibiotics, microbial toxins, heavy metals and serum complement, microbial cultures are most often incubated for hours or days. In these circumstances death and growth occur simultaneously. If additionally some of the cells lyse, e.g. when analysing the serum complement, it is difficult to know to what one should compare the amount of living cells at the, end of the experiment. Convenient methods to determine the number of living cells, e.g. by measuring luciferase bioluminescence, are known but if no more information is available it is impossible to assess to what extent growth or/and death of the micro-organisms takes or has taken place.

Growth rates and death rates of micro-organisms in specific environments are of interest in many areas. Death rates and growth rates of micro-organisms and especially harmful and/or pathogenic micro-organisms are of importance in risk assessments of products of the pharmaceutical industry and products for human consumption with regard to their production, storage and distribution to the consumers. Knowledge of death and growth rates of micro-organisms are of particular importance in specific applications such as in the development of antibiotics, disinfectants and bactericidal products or monitoring of sterilisation, disinfection and cleaning processes.

Reporter genes coding for luminescent or/and fluorescent products have been introduced to micro-organisms to enable the assessment of the quantity or survival of living micro-organisms (WO 96/23898, WO 98/14605, WO 98/30715, WO 98/36081, U.S. Pat. No. 5,824,468). Even simultaneous use of luminescent and fluorescent markers has been used (Fratamico et al., Journal of Food Protection, Vol 50 No 10, 1997, 1167–1173). Luminescent and fluorescent markers have, however, only been used as markers for survival of micro-organisms and the use of two different markers within one micro-organism enabling the differentiation between growth and death rates has not been reported.

OBJECT AND SUMMARY OF THE INVENTION

The object of the present invention is to provide a method to enable the assessment of the growth and death of a micro-organism within a chosen time period in an environment of interest by introducing into said micro-organism at least two reporter genes. The method is characterised in that a) said reporter genes code for luminescent and/or fluorescent products and within said time period and environment at least two said products of the following are produced:

i) an essentially stable product produced in a, within the environment of interest, essentially known proportion to the total amount of cells of said micro-organism that are or have been alive within said chosen time period, ii) a product present in said environment of interest in an essentially known proportion to the amount of cells alive at any moment within said chosen time period and iii) an essentially stable product produced in a, within the environment of interest, essentially known proportion to the total amount of cells of said micro-organism that have died within said chosen time period, and said products can be measured through their luminescence and/or fluorescence;

b) said micro-organism is incubated within the environment of interest and said luminescence and/or fluorescence is detected after said chosen time period, and c) the growth and death rate of the said micro-organism is assessed based on at least two of the following:

i) the known proportion of luminescence or fluorescence to the amount of cells alive after any said chosen time period, ii) the known proportion of luminescence or fluorescence to the total amount of cells that are or have been alive within any said chosen time period, and iii) the known proportion of luminescence or fluorescence to the total amount of cells that have died within any said chosen time period.

DETAILED DESCRIPTION OF THE INVENTION

Figure 1:
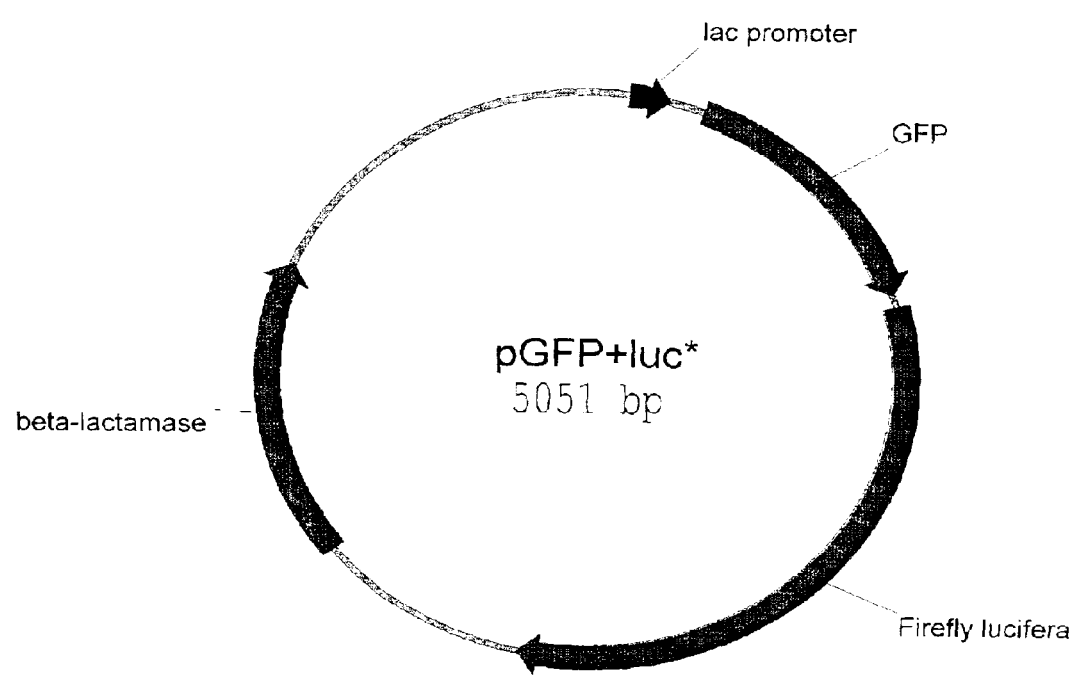
FIG. 1 shows plasmid pGFP+luc* including genes for both GFP and firefly luciferase.

The method according to the present invention can be used to assess the growth and death rate of a micro-organism within a chosen time period in any particular environment of interest. The method is applicable if two different marker genes can be introduced to the micro-organism that code for luminescent and/or fluorescent products, and the products of these fulfil at least two of the following three criteria:

a) a said luminescent product luminesces or said fluorescent product fluoresces in an essentially known proportion to the amount of cells of said micro-organism alive within said chosen time period;

b) a said luminescent product luminesces or said fluorescent product fluoresces in an essentially known proportion to the amount of cells of said micro-organism that are or have been alive within said chosen time period, and c) a said luminescent product luminesces or said fluorescent product fluoresces in an essentially known proportion to the amount of cells of said microorganism that have died within said chosen time period.

In the present application the concept "micro-organism" means any micro-organism into which marker genes can be introduced so, that they will function according to the invention. "Micro-organism" can therefore stand for bacteria, yeast or fungi.

The concept of "introducing a marker gene into a microorganism" means any method by which a marker gene can be made to function within the micro-organism according to the invention. One way of introducing marker genes into micro-organism is by constructing a recombinant strain. This can be done by transforming a strain with a plasmid including the marker genes. An alternative way to introduce reporter genes to bacteria is to utilise transposable elements. In this technique, reporter genes are inserted between insertion sequences in a delivery plasmid. The plasmid is then introduced to a cell by e.g. conjugation of transformation, and once inside the cell, genes surrounded by the insertion sequences are integrated into bacterial chromosome. Integration is stable, i.e. there is no need for a selectable marker such as antibiotic resistance.

Assessment of the growth rate and death rate of a microorganism can be of interest in many specific environments. Within pharmaceutical research the effect of different drugs and candidates for drugs, e.g. antibiotics, on the survival of pathogenic, but also the beneficial micro-organisms of the gut, is of interest. Thus the ultimate interest is in the behaviour of these micro-organisms in a physiological environment affected by drugs.

Another vast area where the possibility of assessing growth and death rate of specific micro-organisms is of interest is that of production, processing, storage and distribution of all products for human consumption. In this area the behaviour of pathogenic or potentially harmful microorganisms in the different environments of the life cycle of these products is of special interest and involves many different aspects such as the influence of temperature, humidity or light and the possible use of preservatives etc.

Additionally growth and death rates of micro-organisms can be of interest for environmental evaluations e.g. when evaluating the effect of emissions into the environment.

Luminescent or fluorescent products coded by reporter genes in different embodiments of this invention can vary as long as their proportion to either the total amount of cells alive, to cells that are or have been alive, or to cells that have died is essentially known. Growth and death rate can be assessed if two of the following: cells alive, cells that are or have been alive, or cells that have died can be determined. Thus luminescence and/or fluorescence measured can be e.g. of a product which is expressed e.g. constitutively or triggered by a specific phase (e.g. replication or death) of the lifecycle of each cell, is stable or labile or which luminescence or fluorescence is dependant on a factor that relates e.g. to a specific phase of the lifecycle of each cell. Depending on the individual characteristics of said product-how produced, stable or labile, possible dependence of its luminescence or fluorescence of said factors etc.—the measured luminescence or fluorescence can be in proportion to one of the three unknown of which two must be known to be able to assess the growth rate and death rate of said cells.

According to one specific embodiment of the invention assessment of the growth and death rate of an *Esherichia coli* strain under the influence of different chemicals or matrixes was enabled by constructing a recombinant strain, which expresses both luciferase and GFP. Altogether the effect of a number of different chemicals and matrixes, such as $CdCl_2$, ethanol, the antibiotics chloramphenicol, rifampicin, and tetracyclin, as well as serum complement on said recombinant *E. coli* strain was tested and found applicable.

The invention will be described in more detail by the following study in which the growth rate and death rate of a recombinant *Esherichia coli* strain, which expresses both luciferase and GFP, is assessed under the influence of ethanol or serum complement.

Summary of the Study

Genes for luciferase and green fluorescent protein have recently raised interest as reporter genes. Luciferase is an enzyme that produces luminescence in the presence of substrate luciferin, molecular oxygen and ATP. Green fluorescent protein (GFP), produces green fluorescence when excited with light. Many mutated forms of GFP have been introduced: some have different excitation and emission wavelengths from the wild type and some mutants form more stable proteins at higher temperatures.

We constructed a recombinant strain of *E. coli*, which expresses both luciferase and GFP. In our construction we used a mutant of GFP, which is more stable at temperatures over +30° C. and it matures quicker than the wild type. Luciferase was from North American firefly, *Photinus pyralis*.

The *E. coli* strain MC1061 was transformed with a plasmid including genes for both GFP and firefly luciferase. FIG. 1 describes the plasmid in general. The sequence of the plasmid is disclosed in the sequence listing. Essential codings of the sequence are as follows:

| | |
|---|---|
| lac promoter | 95–199 |
| GFP | 289–1008 |
| firefly luciferase | 1044–2696 |
| β-lactamase | 3251–4111 |

In our construct, see FIG. 1, the luciferase gene is situated next to the GFP gene and both genes are transcribed in the same direction. The transcription is started at the lac promoter in front of GFP. The lac promoter is constitutively active, because the MC1061 cells lack its repressor. The plasmid also has a gene for ampicillin resistance (β-lactamase).

The transformed *E. coli* strain was propagated under the influence of different concentrations of ethanol or serum complement.

Methods

Growth Conditions

One colony from a pure culture plate was inoculated in 5 ml of LB-medium with ampicillin (100 μg/ml) and grown at +37° C. in a shaker, 250 rpm, for about three hours. After that, the number of cells per milliliter was determined with flow cytometry by using fluorescent spherical latex particles as a reference. One million cells were then removed to an erlenmeyer with 50 ml of LB medium and ampicillin. The culture was grown over night in a shaker, 190 rpm, at room temperature to prevent the culture from growing into the stationary phase during the night. In the morning, the culture was transferred to and grown in a shaker, 330 rpm, until the stationary phase was reached or used after growth at +30° C. for about 1 h to study the influence of ethanol or serum complement as described below.

Influence of Chemicals on the Propagation of E. Coli

The culture obtained as described above was used to study the influence of ethanol or serum complement as follows:

Ethanol

Ethanol (Aa, Primalco Oy) was diluted into pure water to obtain concentrations of 50, 45, 25, 10, 5, 1 and 0% of ethanol when 500 µl of said dilution was added to 500 µl of said culture in an eppendorf tube. The mixture was vortexed and incubated for 5 minutes before measuring fluorescence and luminescence. Live cells were again counted by plating and also by live/dead staining. In the live/dead protocol used the stain cyto 9 stains all cells whereas propidium iodide stains only the dead cells. After staining, cells are passed through a flow cytometer, with which dead and live cells can be differentiated and their proportion determined. (Virta et al. (1998) Appl. Environ. Microbiol. 64: 515–519.)

Serum Complement

The influence of serum complement on the said recombinant E. coli strain was studied using an incubation time of 90 min as described for a different recombinant E. coli strain used in Virta et al. (1998) Appl. Environ. Microbiol. 64: 515–519.

Fluorescence and Luminescence Measurements

The measurements were done with a combined fluoro- and luminometer, Fluoroscan Ascent FL, provided by Labsystems Ltd. (Helsinki, Finland). Cell growth was simultaneously followed with a flow cytometer.

For the measurements, 100 µl of bacterial culture was pipetted into the microtiter plate wells. Fluorescence was measured using 485 nm for excitation and 510 nm for emission. Measuring time was 20 ms. After the fluorescence measurement 100 µl of luciferin in 0.1 M citric acid-sodium citrate buffer (pH 5.0) was dispensed into the wells and the plate was shaken for two minutes (shaking diameter 1 mm, 1 020 rpm), after which luminescence was recorded with a measuring time of 1000 ms.

Plating

Samples for plating were diluted $10^2$ to $10^7$ fold with 150 mM NaCl and plated onto L agar plates (L broth containing 1.6% agar). Colonies were counted after overnight incubation at 37° C.

Live/Dead Staining and Flow Cytometric Analysis

Bacteria from 1 000 µl of cell culture were used for live/dead staining and flow cytometric analysis using a LIVE/DEAD BacLight bacterial viability kit (catalogue no. L-7005) for microscopy and quantitative analysis obtained from Molecular Probes Europe (Leiden, The Netherlands) and Fluoresbrite beads (diameter, 1.8 µm) obtained from Polysciences Inc. (Warrington, Pa.) as described in Virta et al. (1998) Appl. Environ. Microbiol. 64: 515–519.

Results

When the cultures were transferred to +30° C., the cells grew logarithmically for 14 hours depending on the initial cell concentration. Luminescence and fluorescence rose logarithmically and were essentially constant per cell. Thus cell number could be assessed based on luminescence or fluorescence.

Figure 2:
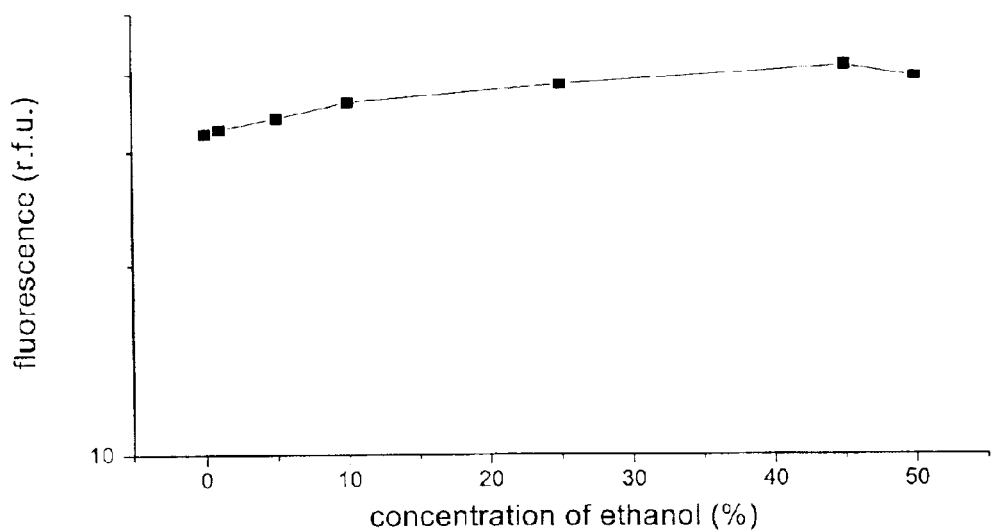
FIG. 2 shows fluorescence during growth phase of E. coli with plasmid pGFP+luc* at 30° C. as a function of the concentration of ethanol in the cell culture.
Figure 3:
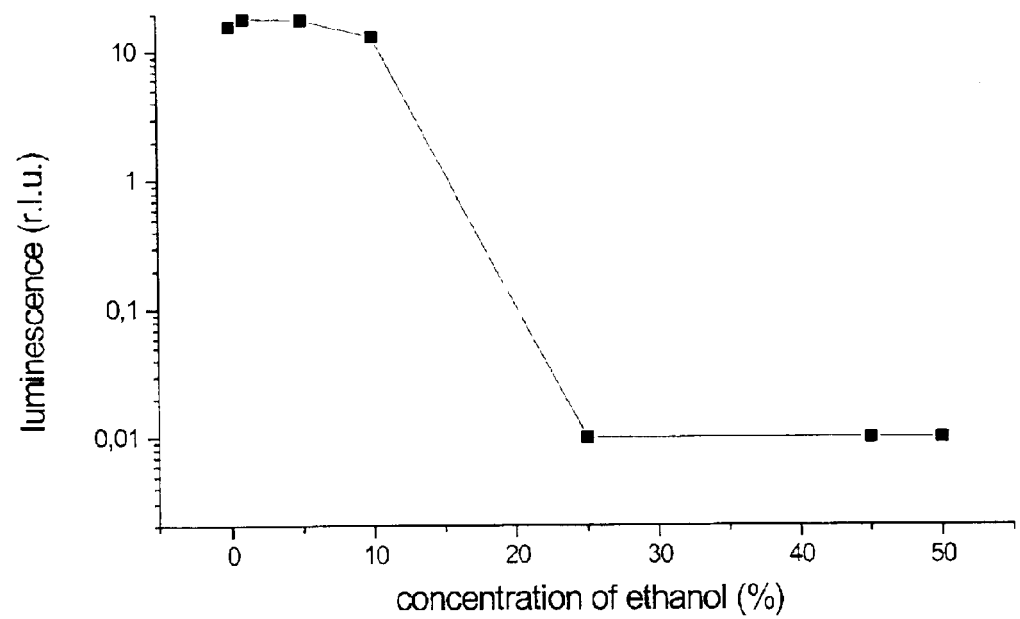
FIG. 3 shows luminescence during growth phase of E. coli with plasmid pGFP+luc* at 30° C. as a function of the concentration of ethanol in the cell culture.
Figure 4:
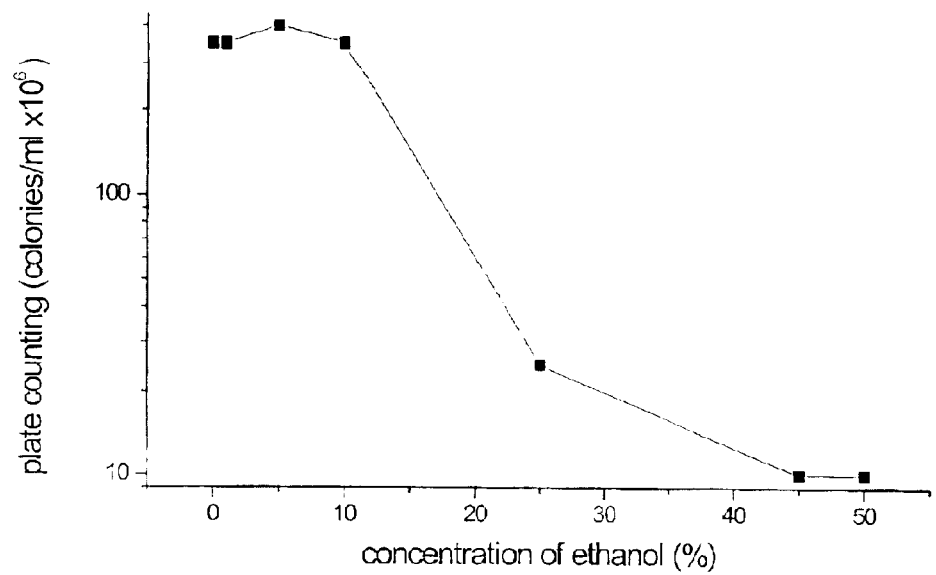
FIG. 4 shows the amount of living cells, i.e. colony forming units, according to plating during growth phase of E. coli with plasmid pGFP+luc* at 30° C. as a function of the concentration of ethanol in the cell culture.
Figure 5:
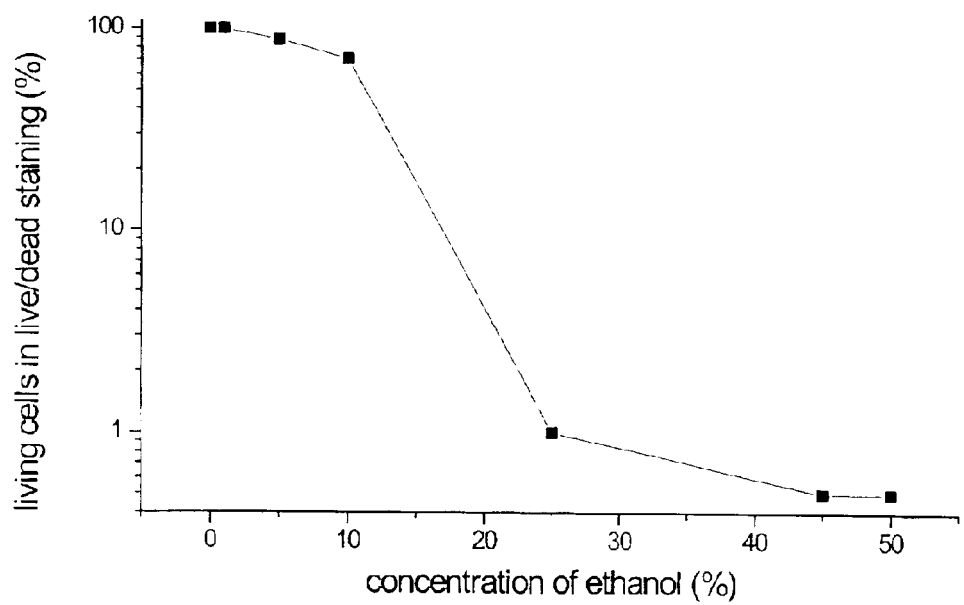
FIG. 5 shows the percentage of living cells according to live/dead staining and flow cytometric analysis during growth phase of E. coli with plasmid pGFP+luc* at 30° C. as a function of the concentration of ethanol in the cell culture.

When ethanol was added in different concentrations to the growth medium (see FIGS. 4 and 5) death was, after a very short incubation period of 5 min, more or less unsignificant at ethanol concentrations below 5% and became more significant with increasing ethanol concentration reaching very pronounced significance at ethanol concentrations above 10%. Correspondingly fluorescence (FIG. 2) was essentially constant whatever the ethanol concentration in spite of dramatically decreasing corresponding live cell count according to plate count (FIG. 4) and percentage of live cells according to the live/dead staining (FIG. 5) whereas luminescence (FIG. 3) dropped dramatically essentially corresponding to the dramatic drop in plate count (FIG. 4) and the percentage of live cells (FIG. 5) with increased ethanol concentration.

Figure 6:
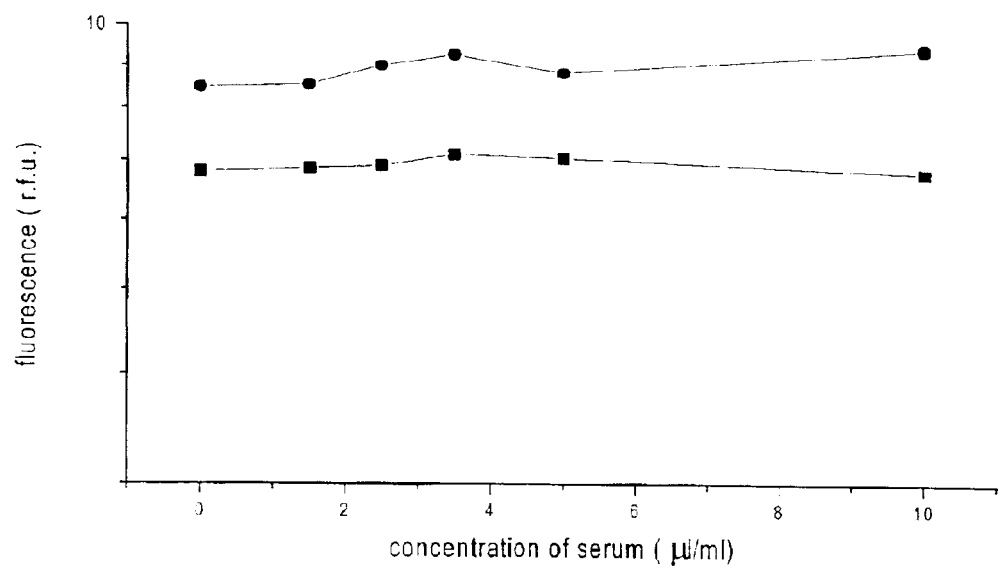
FIG. 6 shows fluorescence before (squares) and after (circles) incubation with serum complement during growth phase of E. Coli with plasmid pGFP+luc* at 30° C. as a function of the concentration of serum complement in the cell culture.
Figure 7:
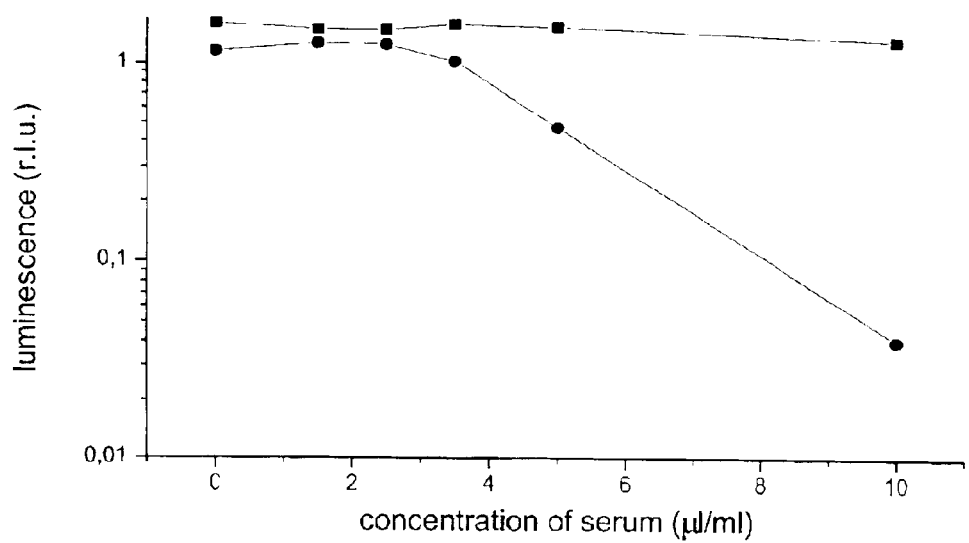
FIG. 7 shows luminescence before (squares) and after (circles) incubation with serum complement during growth phase of E. coli with plasmid pGFP+luc* at 30° C. as a function of the concentration of serum complement in the cell culture.
Figure 8:
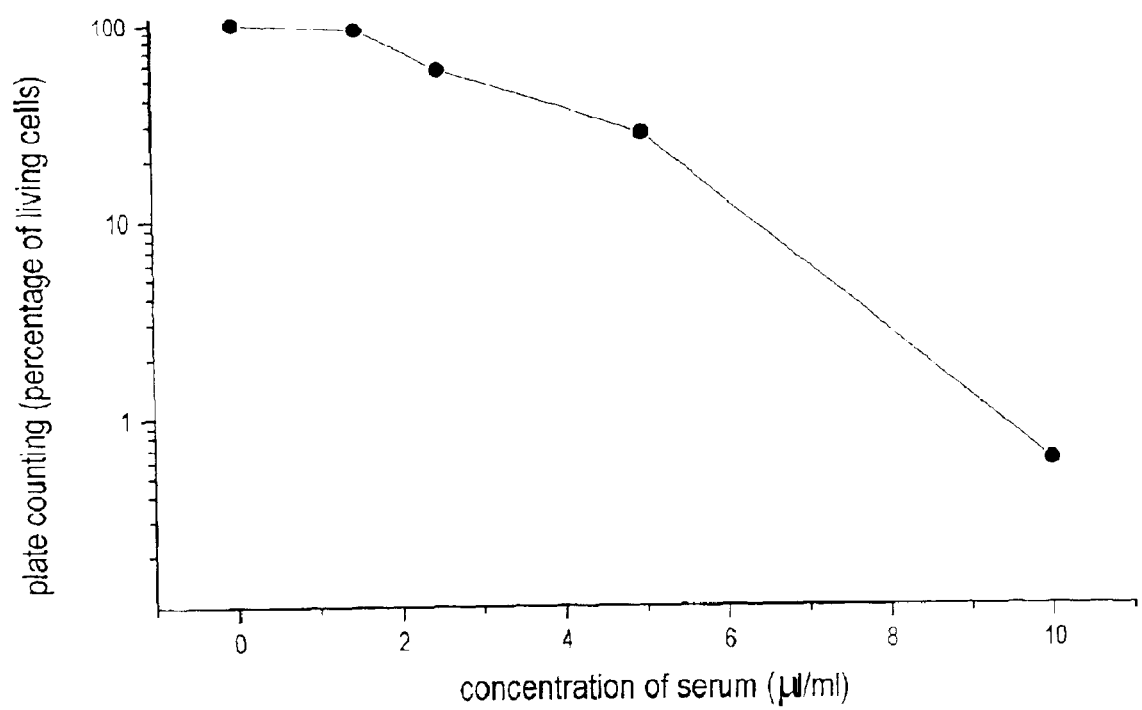
FIG. 8 shows the percentage of living cells according to plating during growth phase of E. coli with plasmid pGFP+luc* at 30° C. as a function of the concentration of serum complement in the cell culture.

The effect of serum complement on the growth and death of E. coli is shown in FIGS. 6 to 8. Fluorescence (FIG. 6) and luminescence (FIG. 7) are shown before (squares) and after (circles) incubation for 90 minutes with serum complement. Fluorescence (FIG. 6) is slightly increased, during incubation regardless of the concentration of serum, whereas luminescence (FIG. 7) decreases during incubation with increasing serum concentration. The decrease of luminescence during incubation with increasing concentrations of serum correlates clearly with the percentage of cells alive after incubation (FIG. 8).

What is claimed is:

1. A method to enable the assessment of the growth rate and death rate of a micro-organism within a chosen time period in an environment of interest comprising introducing into said micro-organism at least two reporter genes, wherein
   a) said reporter genes code for luminescent and/or fluorescent products and within said time period and environment producing at least two said products of the following:
      i) a stable product produced in step (a), within the environment of interest, essentially known proportion to the total amount of cells if said microorganism that are or have been alive within said chosen time period,
      ii) a product present in said environment of interest in an essentially known proportion to the amount of cells alive at any moment within said chosen time period, and
      iii) a stable product produced in step (a), within the environment of interest, essentially known proportion to the total amount of cells of said micro organism that have died within said chosen time period, and said products can be measured through their luminescence and/or fluorescence;
   b) incubating said micro-organism within the environment of interest and detecting said luminescence and/or fluorescence after said chosen time period, and
   c) assessing the growth and death rate of the said micro-organism based on measuring at least two of the following:
      i) the known proportion of luminescence or fluorescence to the amount of cells alive after any said chosen time period,
      ii) the known proportion of luminescence or fluorescence to the total amount of cells that are or have been alive within any said chosen time period, and
      iii) the known proportion of luminescence or fluorescence to the total amount of cells that have died within any said chosen time period.

2. The method according to claim 1 wherein said micro-organism is a gram negative bacteria.

3. The method according to claim 1 wherein
   a) one reporter gene coding for a luminescent product is luciferase, which is used for the determination of amount of cells alive at any moment within said chosen time period, and
   b) another reporter gene coding for a fluorescent product is green fluorescent protein (GFP), which is used for the determination of total amount of cells of said micro organism that are or have been alive within said chosen time period.

4. The method according to claim 1 wherein said reporter genes are introduced into said micro-organism in a plasmid.

5. The method according to claim 3 wherein said plasmid is pGFP+luc* (SEQ ID NO: 1).

6. The method according to claim 2 wherein
   a) one reporter gene coding for a luminescent product is luciferase, which is used for the determination of amount of cells alive at any moment within said chosen time period, and
   b) another reporter gene coding for a fluorescent product is green fluorescent protein (GFP), which is used for the determination of total amount of cells of said micro organism that are or have been alive within said chosen time period.

7. The method according to claim 2 wherein said reporter genes are introduced into said micro-organism in a plasmid.

8. The method according to claim 4 wherein said plasmid is pGFP+luc* (SEQ ID NO: 1).

9. The method according to claim 6 wherein said plasmid is pGFP+luc* (SEQ ID NO: 1).

10. The method according to claim 7 wherein said plasmid is pGFP+luc* (SEQ ID NO: 1).

* * * * *